United States Patent
Byerly et al.

(10) Patent No.: US 9,149,578 B2
(45) Date of Patent: Oct. 6, 2015

(54) NEEDLE CARTRIDGE FOR MEDICATION INJECTION DEVICE

(75) Inventors: Roy Howard Byerly, Indianapolis, IN (US); Ilario Melzi, Milan (IT)

(73) Assignee: Eli Lilly and Company, Indianapolis, IN (US)

(*) Notice: Subject to any disclaimer, the term of this patent is extended or adjusted under 35 U.S.C. 154(b) by 782 days.

(21) Appl. No.: 13/298,318

(22) Filed: Nov. 17, 2011

(65) Prior Publication Data

US 2012/0130313 A1    May 24, 2012

Related U.S. Application Data

(60) Provisional application No. 61/415,458, filed on Nov. 19, 2010.

(51) Int. Cl.
| | |
|---|---|
| *A61M 5/32* | (2006.01) |
| *A61M 5/20* | (2006.01) |
| *A61B 5/151* | (2006.01) |
| *A61M 5/00* | (2006.01) |
| *A61M 5/34* | (2006.01) |
| *A61M 5/142* | (2006.01) |
| *A61M 5/158* | (2006.01) |

(52) U.S. Cl.
CPC .............. *A61M 5/20* (2013.01); *A61B 5/15146* (2013.01); *A61M 5/008* (2013.01); *A61M 5/322* (2013.01); *A61M 5/3287* (2013.01); *A61M 5/3293* (2013.01); *A61M 5/349* (2013.01); *A61M 2005/004* (2013.01); *A61M 2005/14252* (2013.01); *A61M 2005/1581* (2013.01)

(58) Field of Classification Search
CPC .......... A61M 2005/004; A61M 5/008; A61B 5/15146

USPC .................... 604/232, 82, 171, 173; 606/181; 206/366
See application file for complete search history.

(56) References Cited

U.S. PATENT DOCUMENTS

| | | | |
|---|---|---|---|
| 4,203,518 A * | 5/1980 | Current | .......................... 206/380 |
| 5,224,596 A | 7/1993 | Kruger | |
| 5,285,896 A | 2/1994 | Salatka et al. | |

(Continued)

FOREIGN PATENT DOCUMENTS

| | | |
|---|---|---|
| WO | 0187388 | 11/2001 |
| WO | 0193927 | 12/2001 |

(Continued)

OTHER PUBLICATIONS

Roche Diagnostics, Accu-Chek Multiclix Lancing Device website form Apr. 13, 2007.

*Primary Examiner* — Nicholas Lucchesi
*Assistant Examiner* — Anh Bui
(74) *Attorney, Agent, or Firm* — Edward J. Prein

(57) ABSTRACT

A cartridge with injection needles for an injection device. The cartridge includes a plurality of injection needle assemblies, each including a hub, mounted to be shiftable in cavities of a needle assembly support. A hub ledge having a drive member engageable push surface projects within a gap between a first hub portion and a second hub portion. Driving engagement of the push surface by an injection device drive member shifts the needle assembly from a retracted position to an injection position, during which shifting the second hub portion moves relative to the first hub portion. A pull surface on the second hub portion is engagable with the drive member for lifting the needle assembly from the injection position.

5 Claims, 17 Drawing Sheets

(56) References Cited

U.S. PATENT DOCUMENTS

| | | | |
|---|---|---|---|
| 5,545,145 A * | 8/1996 | Clinton et al. | 604/192 |
| 5,569,190 A * | 10/1996 | D'Antonio | 604/72 |
| 5,775,498 A * | 7/1998 | Kashanchi | 206/364 |
| 5,829,589 A * | 11/1998 | Nguyen et al. | 206/366 |
| 5,873,462 A * | 2/1999 | Nguyen et al. | 206/366 |
| 6,032,543 A * | 3/2000 | Årthun et al. | 73/863.84 |
| 6,325,241 B1 | 12/2001 | Garde et al. | |
| 6,346,094 B2 * | 2/2002 | West et al. | 604/241 |
| 6,616,616 B2 * | 9/2003 | Fritz et al. | 600/583 |
| 6,723,068 B2 * | 4/2004 | Lavi et al. | 604/82 |
| 7,004,928 B2 | 2/2006 | Aceti et al. | |
| 7,025,774 B2 | 4/2006 | Freeman et al. | |
| 7,361,163 B2 * | 4/2008 | Cohen | 604/232 |
| 2002/0169416 A1 * | 11/2002 | Gonnelli et al. | 604/142 |
| 2004/0260325 A1 * | 12/2004 | Kuhr et al. | 606/181 |
| 2005/0149090 A1 * | 7/2005 | Morita et al. | 606/181 |
| 2005/0154410 A1 * | 7/2005 | Conway et al. | 606/181 |
| 2005/0234494 A1 * | 10/2005 | Conway et al. | 606/181 |
| 2006/0264996 A1 | 11/2006 | LeVaughn et al. | |
| 2011/0023644 A1 * | 2/2011 | Ramadoss et al. | 74/425 |

FOREIGN PATENT DOCUMENTS

| | | |
|---|---|---|
| WO | 0200101 | 1/2002 |
| WO | 0211797 | 2/2002 |
| WO | 0211798 | 2/2002 |
| WO | 02100465 | 12/2002 |
| WO | 2004030726 | 4/2004 |
| WO | 2005002649 | 1/2005 |
| WO | 2005018709 | 3/2005 |
| WO | 2005097237 | 10/2005 |
| WO | 2006004859 | 1/2006 |
| WO | 2007143323 | 12/2007 |
| WO | 2008150715 | 12/2008 |
| WO | 2009016161 | 2/2009 |
| WO | 2010084113 | 7/2010 |

* cited by examiner

NEEDLE CARTRIDGE FOR MEDICATION INJECTION DEVICE

BACKGROUND OF THE INVENTION

The present invention pertains to medical devices, and, in particular, to a cartridge with injection needles for a medication injection device.

A wide variety of medication injection devices are available which allow people, such as patients or health care professionals, to administer pharmaceuticals to themselves or others. Many of these devices are considered reusable, but utilize disposable injection needles as well as disposable medication cartridges, which medication cartridges each hold one or more doses of the desired pharmaceutical.

One type of known injection device is disclosed in International Publication Number WO 2005/097237, which device utilizes a disposable needle cassette or cartridge that contains a multitude of single use injection needles. Modifications to the needle cassette or cartridge are disclosed in International Publication Number WO 2008/150715, including a modification in the design of the injection needle assembly that offered, among other things, an advantage related to injection needle retraction. While functional, these needle cartridges were not without their shortcomings For example, the height of the cartridge attributable to the design of the needle assemblies contributed to the overall profile of the injection device being larger than may be desired for an associated injection device having a given feature set.

Thus, it would be desirable to provide a cartridge for injection needles which is suitable for beneficial use while overcoming one or more shortcomings of the prior art.

BRIEF SUMMARY OF THE INVENTION

In one form thereof, the present invention provides a cartridge for a medication injection device having a reciprocating drive member, the cartridge including a plurality of injection needle assemblies, each injection needle assembly including a hub and a needle, each needle including a first leg segment with a first end and a second leg segment with a second end and a spanning segment, the spanning segment providing fluid communication between portions of the first leg segment and the second leg segment opposite the first and second ends, the first end and second end of each needle both facing in a first direction, each hub including a first portion and a second portion, the needle supported in the first hub portion, the second hub portion movable relative to the first hub portion between a ready arrangement and a needle assembly lifting arrangement. The cartridge also includes a needle assembly support defining a plurality of mutually parallel, needle assembly accommodating cavities, each injection needle assembly mounted in a different one of the plurality of needle accommodating cavities to be shiftable in the first direction from a retracted position, at which the first and second ends both are disposed within the cavity, to an injection position, at which the first and second ends both project outside of the cavity, the needle assembly support loadable into the injection device to be movable therein to allow for separate operational alignment of each injection needle assembly with the drive member of the injection device, whereby the drive member may move to drivingly engage the hub of an operationally aligned needle assembly so as to shift that needle assembly from the retracted position to the injection position. Each needle assembly is structured and arranged with the needle assembly support for its second hub portion to be moved relative to its first hub portion from the ready arrangement to the needle lifting arrangement upon a shifting of that needle assembly from the retracted position to the injection position. Each second hub portion includes a pull surface engagable with the drive member during needle assembly lifting. For a given needle assembly in alignment for operational engagement with the drive member, and when the drive member drivingly engages the hub of that given needle assembly, the second hub portion pull surface, in a second direction opposite the first direction, is located clear of the drive member when the given needle assembly is disposed in the retracted position with the second hub portion in the ready arrangement. For that given needle assembly, the second hub portion pull surface, in the second direction, is located adjacent the drive member when the given needle assembly has been shifted to the delivery position by the hub being engaged by the drive member moving in the first direction, whereby the given needle assembly is liftable in the second direction by engagement of the pull surface of the second hub portion in the needle assembly lifting arrangement by the drive member when the drive member returns in the second direction. The improvement to the cartridge includes a hub ledge having a drive member engageable push surface projecting within a gap between the first hub portion and the second hub portion, and wherein the second hub portion pull surface, when the second hub portion is in the needle assembly lifting arrangement, is disposed at a height in the first direction below a height of a furthermost extent of the first hub portion in the second direction.

One advantage of the present invention is that a cartridge may be provided having needle assemblies that function with a low profile configuration.

Another advantage of the present invention is that a cartridge may be provided having needle assemblies that may be less likely to shift to cause needle exposure during handling of the cartridge.

Another advantage of the present invention is that a cartridge may be provided having needle assemblies that when in the fully extended position during use resist tilting that could otherwise lead to leakage through a medication cartridge septum.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
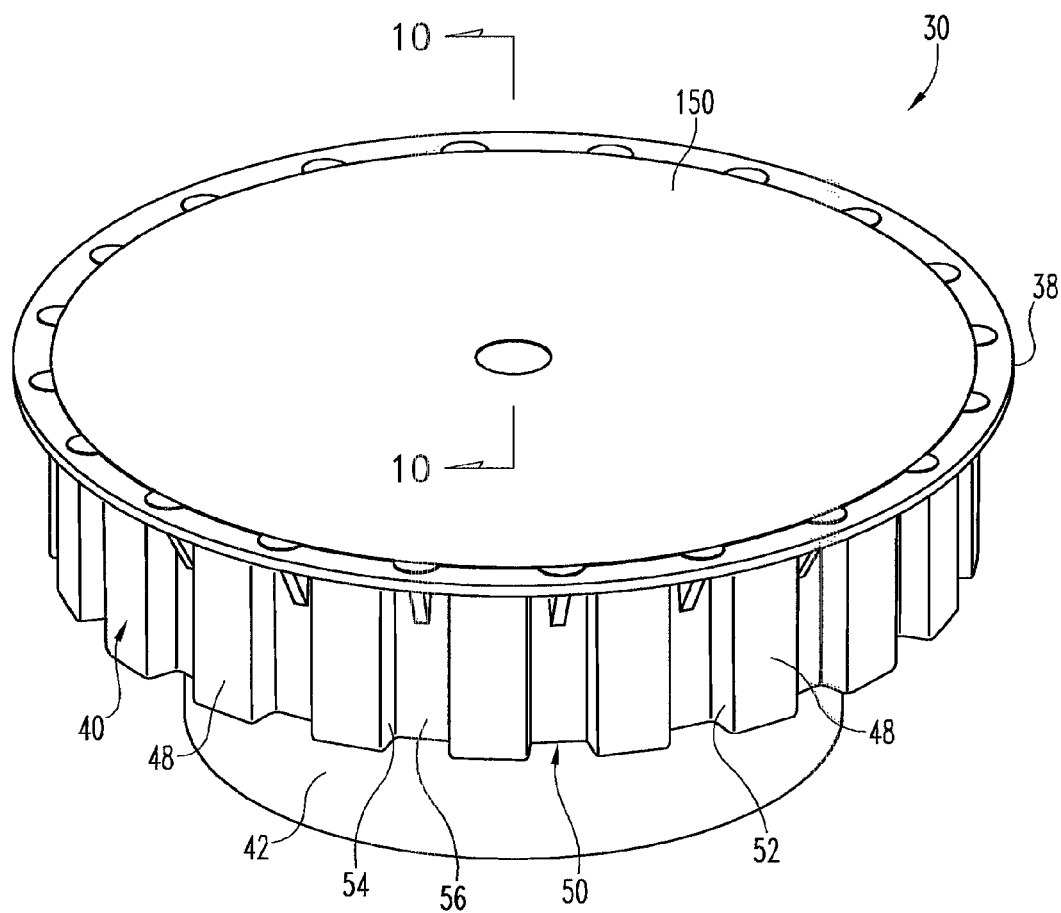
FIG. 1 is a top perspective view of a first embodiment of a cartridge with injection needle assemblies of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
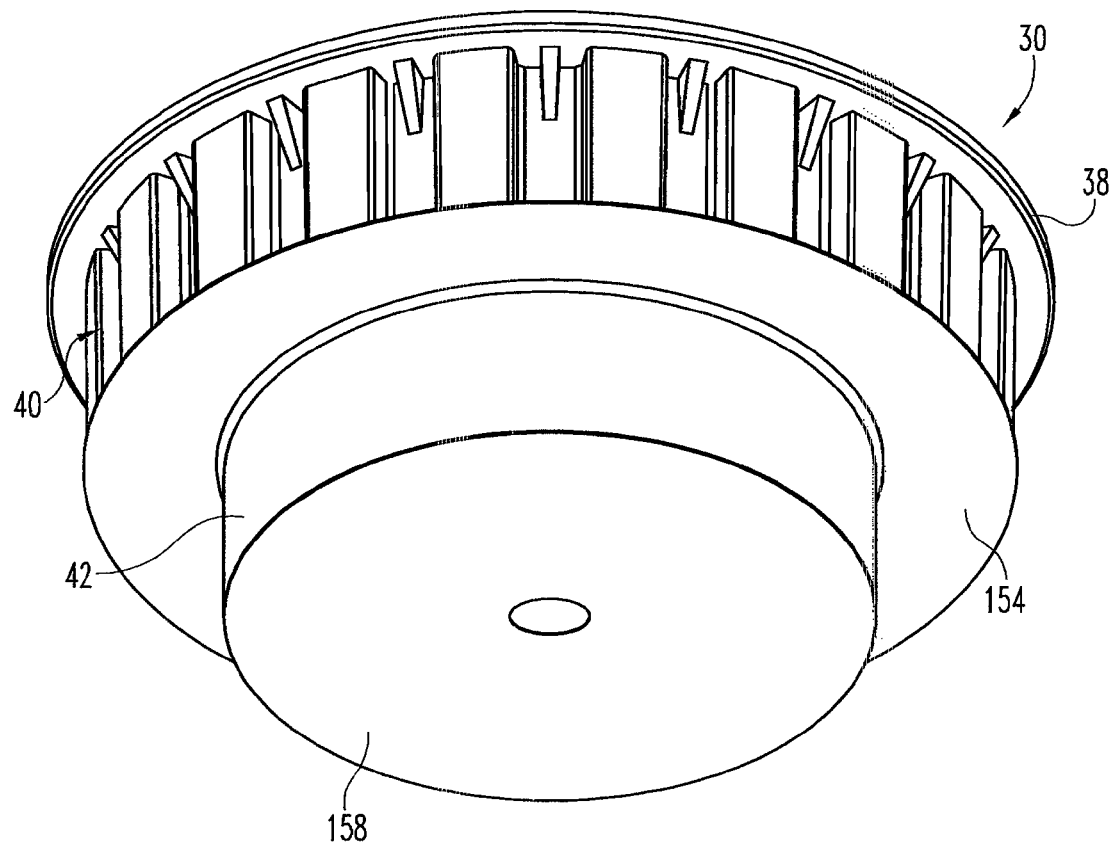
FIG. 2 is a bottom perspective view of the cartridge with needle assemblies of FIG. 1.
Figure 3:
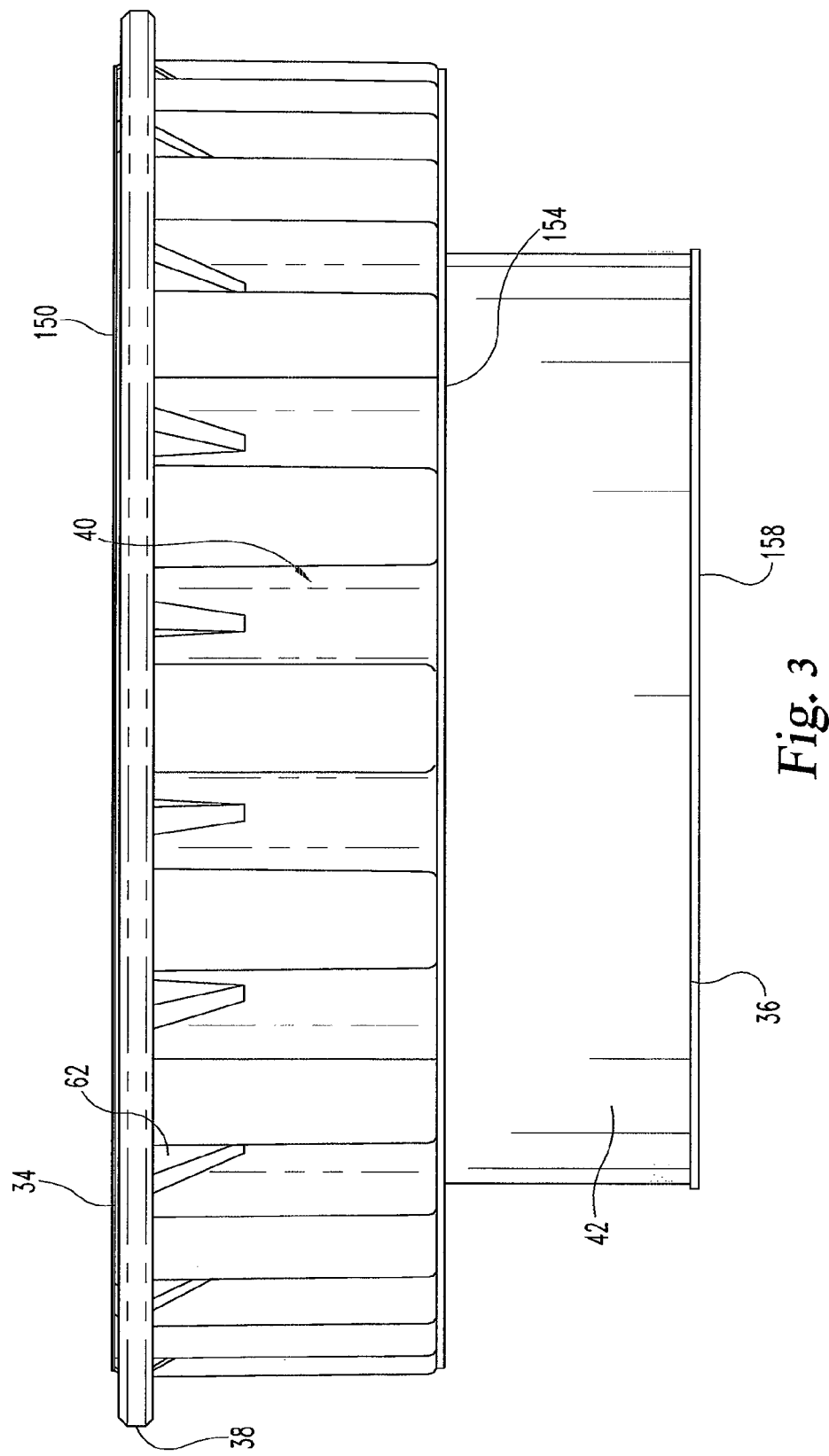
FIG. 3 is a side view of the cartridge with needle assemblies of FIG. 1.
Figure 4:
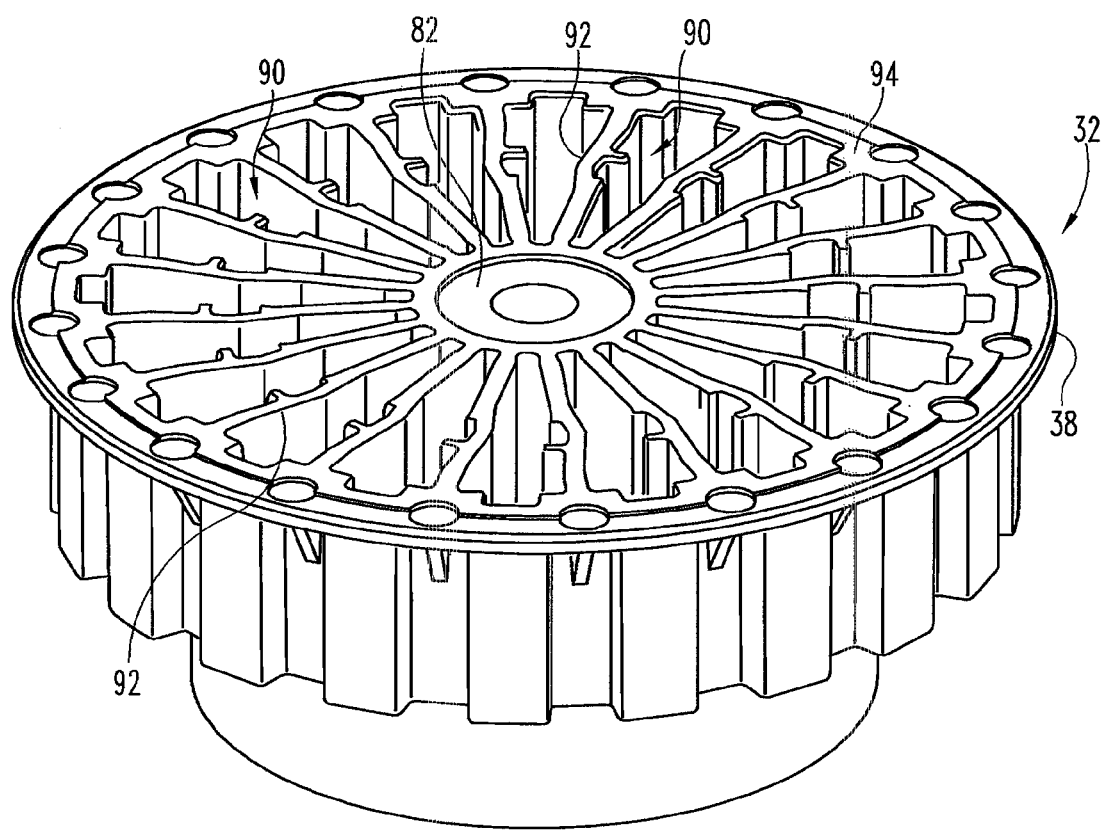
FIG. 4 is a top perspective view of the cartridge with injection needle assemblies of FIG. 1, wherein its complement of needle assemblies as well as the sterility-maintaining membranes are not shown.
Figure 5:
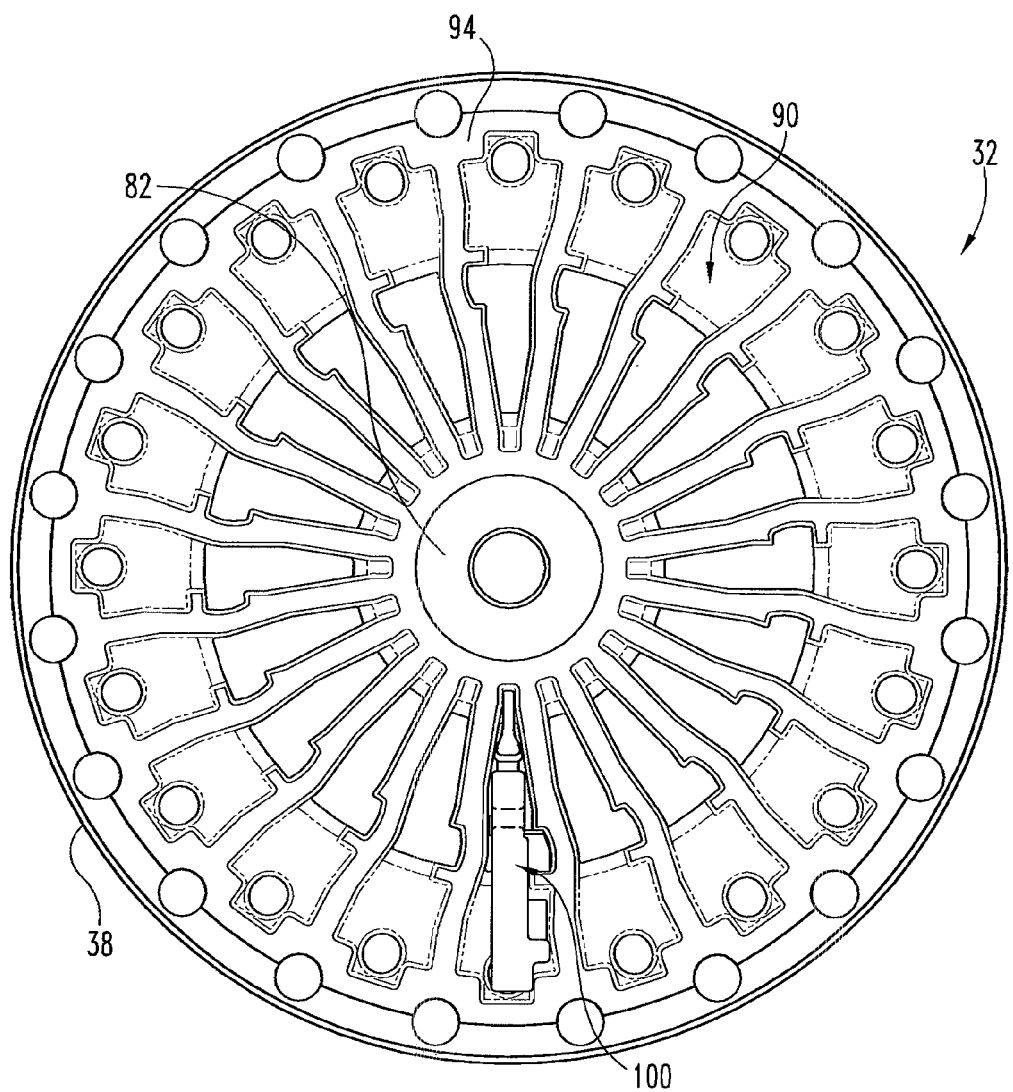
FIG. 5 is a top view of the cartridge of FIG. 4, wherein only a single needle assembly is further shown.

With initial reference to FIGS. 1, 2 and 3, there is shown a first embodiment of a cartridge with injection needle assemblies of the present invention, which cartridge with needles is generally designated 30. Cartridge 30 is similar in numerous respects to the designs disclosed in International Publication Number WO 2008/150715, which application is incorporated herein by reference. Cartridge 30 is particularly structured so as to be compatible with an injection device that may be similar in overall functionality to that disclosed in International Publication Number WO 2005/097237. Some possible differences in such injection device will be apparent from the following disclosure with respect to cartridge 30. However, details of such injection device provided herein are in furtherance of an understanding of cartridge 30 and are not limiting, as the injection device itself is not a part of the inventive cartridge.

Cartridge 30 includes a base or support in which the injection needles are shiftably mounted. The support is shown provided in the form of a carousel 32 that is formed as a single piece, such as injection molded out of a durable and rigid plastic material such as ABS. Carousel 32 is sized and configured to be loadable by a user into an injection device. When so loaded, the carousel 32 is rotatable therein by an indexing mechanism, not shown, of the injection device to allow for separate operational alignment of each injection needle assembly with a single reciprocating drive member of the injection device, which drive member's reciprocating movement is down and then up to effect needle extension from the device and needle withdrawal or return into the device. The axis of rotation of the carousel within the injection device is parallel to the direction in which the injection needle assemblies of the cartridge are individually shiftable by the reciprocating drive member during use.

Carousel 32 includes a generally flat top 34 and a generally flat bottom 36. Top and bottom, above and below, upper and lower, and any other directional or spatial references are used herein to provide a frame of reference that facilitates an understanding of the invention. It contemplates an orientation of the cartridge when loaded in an injection device, and with that injection device being rested or placed upon, and ready to insert the injection needle vertically during the injection process into, a flat, horizontal surface. As the injection device with which the instant cartridge is used may be operated in other than this rest orientation, such as for use to inject into the abdomen of a patient sitting upright in which case the flat top 34 of the carousel at the time of injection would be vertically oriented and facing to the side and away from the patient's abdomen, the directional references herein are not intended to be limiting to a particular orientation for use.

Figure 9:
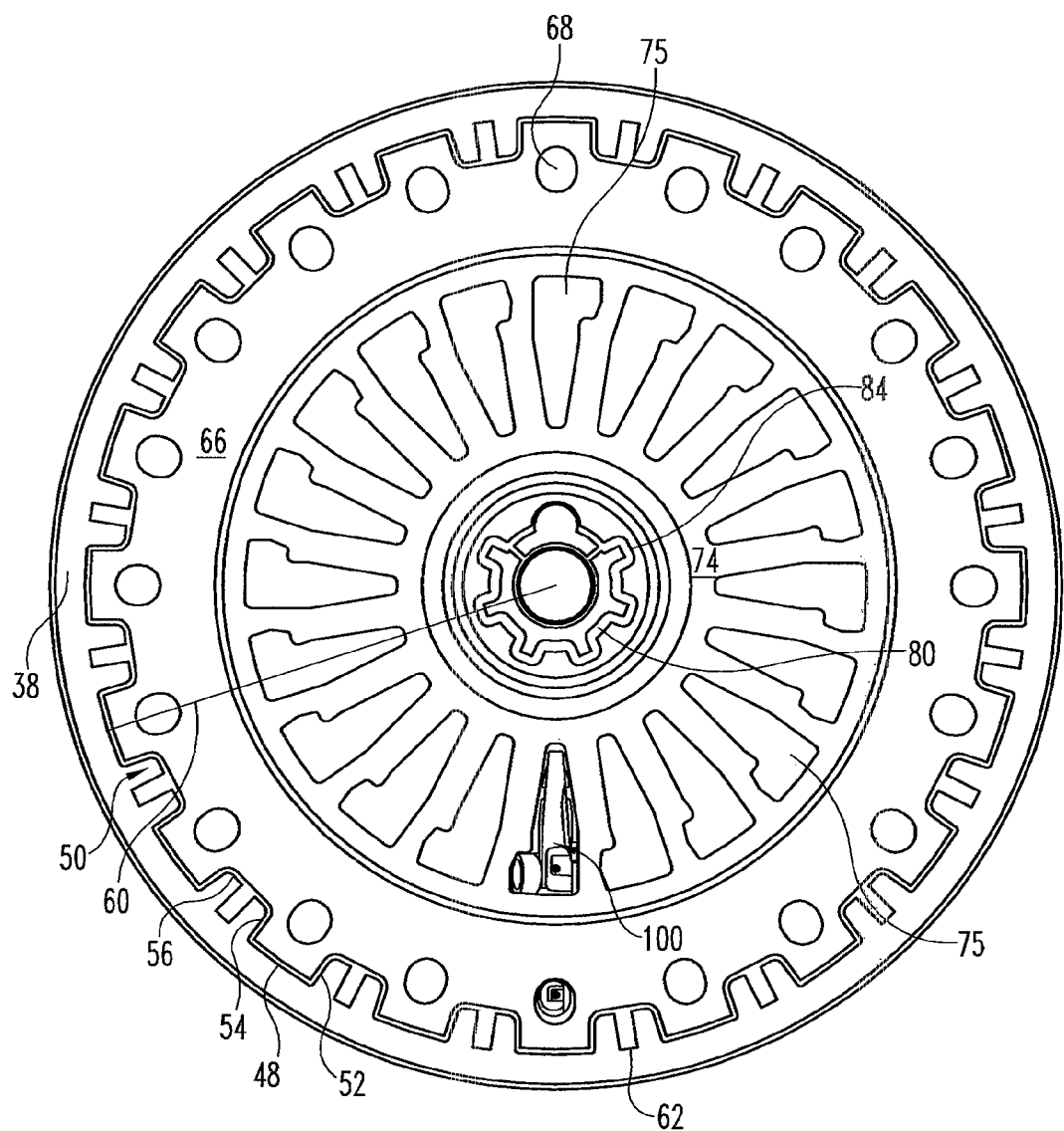
FIG. 9 is a bottom view of the cartridge including the single needle assembly of FIG. 5.

The outer radial periphery of carousel 32 extending from top 34 to bottom 36 includes a flange or rim 38, a notched wall region 40, and a lower wall region 42. Flange 38 is continuous around the carousel perimeter and radially overhangs the outermost extent of wall region 40 to provide a mounting rim. The mounting rim 38 slidably fits within a suitable track provided in the not shown injection device. When a user inserts rim 38 in the track to removably mount the cartridge 30 within the injection device, the rim is vertically captured within the track, thereby maintaining the carousel in a fixed vertical spaced relationship with a medication containing cartridge held within the injection device Wall region 40 allows for a rotational indexing of the carousel within the injection device. Wall region 40 includes an outer radial periphery that is substantially cylindrical with interruptions to such shape provided by longitudinally arranged notches at even angular intervals around the entire circumference. The periphery includes generally rectangular-shaped land regions 48 connected by recessed surfaces, generally designated 50. Each set of recessed surfaces 50 defines a notch to the cylindrical periphery and has a generally squared U-shape as viewed in a cross-section perpendicular to the axis of the cylindrical periphery, which U-shape is readily visible in FIG. 9.

Recessed surfaces 50 each include wall surfaces 52 and 54 that flank a base surface 56. Wall surfaces 52 and 54 are mirror images of each other. In a device where the cartridge 30 is intended to be rotated therein in a couterclockwise direction from the perspective of a viewer observing the top of the cartridge, wall surface 54 within a given notch forms the leading edge of a land region 48, while the wall surface 52 of the successive notch in the clockwise direction, as viewed from above, forms the trailing edge of that same land region 48.

Figure 8:
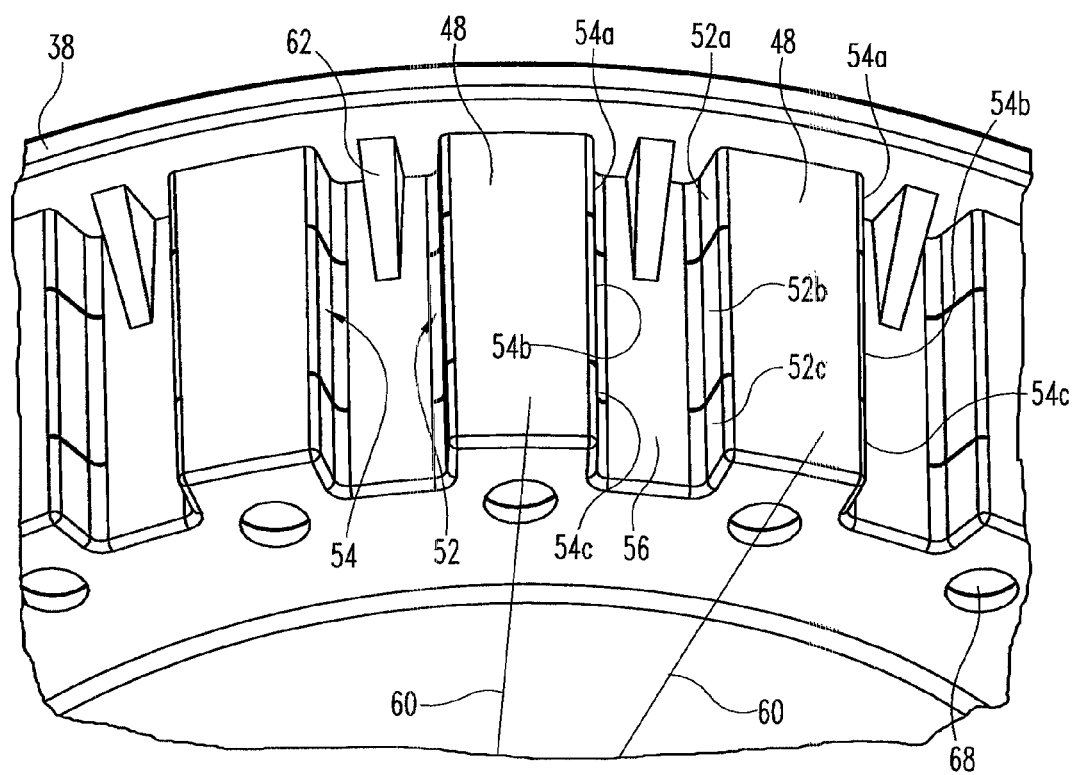
FIG. 8 is a further, partial perspective view of the cartridge with injection needle assemblies of FIG. 7, wherein the molding draft is further shown.

With particular reference to FIG. 8, wall surfaces 52 and 54 are shown each being of three distinct regions that is to facilitate one method of their molding while providing desired indexing characteristics. Each wall surface 52 in a vertical direction includes regions 52a, 52b and 52c, and each wall surface 54 similarly includes regions 54a, 54b and 54c.

Each pair of wall surface region 54b and wall surface region 52b that form portions of the leading and trailing edges of a given land region 48 are straight along their respective width, such width extending in the radial direction. In addition, such wall surface regions 52b and 54b are oriented generally parallel to a line, shown at 60, extending between the angular center of the given land region 48 and the center of the carousel, that is a radial line of the cartridge which bisects the angular length of the given land region. The effectively squarish configuration of the ends of land regions 48 resulting from their associated parallel wall surface regions 52b and 54b produces a protrusion that is more accurately indexable. While this parallel orientation provides a precise indexing of the cartridge, exact parallelism is not required but may be altered such as by being at small angles of up to five degrees from parallel while still providing highly desirable precision. These regions 52b and 54b are designed to be directly contacted by the injection device indexing mechanism, and their parallel relationship with the land region bisector 60 need only be provided along the portion of their respective radial widths intended to be directly contacted by the indexing mechanism.

The indexing mechanism of the injection device is not shown but may be in the form of a screw drive element having a cartridge-engaging thread. The screw thread fits within the notches between land regions 48, and when the screw drive element rotates the thread pushes against the trailing surface region 52b of an adjacent land region to rotate the cartridge 30 within the injection device. The thread has a discontinuity along its length into which fits the next land region 48 as the screw drive element rotation continues, and when the needle cartridge has been properly indexed to its next operational alignment, the screw thread flanks the leading surface region 54b and trailing surface region 52b of the next land region 48. The indexing mechanism may be offset from the reciprocating drive member of the injection device, and as a result the indexing mechanism may contact surface regions 52b and 54b angularly spaced, such as about ninety degrees, around the cartridge from the needle assembly to be engaged by the reciprocating drive member for the instant injection.

Wall surface regions 52a and 52c and wall surface regions 54a and 54c are provided with draft to facilitate injection molding when an axially moving mold is employed. For example, wall surface regions 52a and 54a project slightly farther into the notch than wall surfaces regions 52b and 54b, and wall surface region 52c and 54c are undercut slightly into the land as compared to wall surface regions 52b and 54b, to allow mold elements to insert from below to form surfaces 52 and 54 during molding. Wall region 40 includes gussets 62 extending from base surfaces 56 to a point radially coextensive with land regions 48 to provide strength to the carousel 32 and its rim 38. Gussets 62 do not interfere with the portions of the device that engage rim 38, and also do not interfere with the indexing mechanism of the injection device as the gussets are disposed above the regions 52b and 54b of the wall surfaces 52 and 54 directly engaged by such indexer.

Extending radially inward from the lower edge of wall region 40 is a generally annular flange 65 of the carousel. The underside 66 of flange 65 faces directly downward and is oriented transverse to the rotational axis of the carousel. Flange 65 includes needle accommodating openings or ports 68 sized to provide clearance for the needle and hub of the injection needle assembly. Each opening 68 is slightly oval and disposed radially inward of a different land region 48 along that land region's respective centerline 60.

Lower wall region 42 depends from the inner radial periphery of flange 65 and includes a cylindrical outer radial periphery 71. Wall region 42 is intended to be engaged by complementarily shaped spring arms (not shown) of the injection device, which spring arms aid in locating and retaining the cartridge 30, in a horizontal direction, in a V-shaped structure within the device that accommodates the cartridge when it is loaded in the device for use.

The interior volume of lower wall region 42 has a lower surface 74 that forms the carousel bottom 36. Needle accommodating openings or ports 75 are provided in surface 74, and each opening 75 is disposed radially inward of a different opening 68.

The inner periphery of the interior volume of wall region 42 defines a circular cylindrical opening 73 in which is centered a tubular column 80 that provides features used in manufacturing. Column 80 depends from a recessed, apertured central region 82 proximate the top of surface 34 and is shown at 84 as having a finned form along its length to provide high rigidity while being of a common wall thickness for molding purposes. A discontinuity in column 80 shown at 86 is not functional but rather results from the molding process.

The interior volume of carousel 32 is formed with hollows or cavities, each generally designated 90. Carousel 32 is intended for use in twenty injections and includes twenty cavities 90, all of which are identical and located at equal angular intervals around the carousel circumference. The vertical orientation of each cavity 90 is parallel to the vertical orientation of the other cavities 90. Although only one needle assembly, generally designated 100, is shown in various of the Figures, to allow for twenty injections carousel 32 is equipped with twenty identical needle assemblies 100 each intended for a single use, resulting in each cavity being fitted with its own injection needle assembly.

Each cavity 90 opens or ports to the same three planar surfaces on the carousel exterior, namely top surface 94, flange surface 66, and bottom surface 74. Each cavity 90 has a mouth portion 92 that opens to the planar, upwardly facing top surface 94. Mouth portion 92 is sized and shaped to allow insertion of the needle assembly 100 into cavity 90 during manufacture, as well as allow operational engagement of the contained injection needle assembly 100 by the drive member or hammer of the injection device as more fully described below. Top surface 94 with its mouth portions 92 forms a major part of the cartridge top 34 and top surface 94 and is slightly vertically offset above rim 38 and recessed region 82. This offsetting promotes a suitable sealing of the sealing membrane to the carousel top surface 94 during manufacture.

The port 68 of each cavity 90 provided in the planar flange surface 66 is oval shaped to allow passage therethrough of a needle tip of an injection needle assembly, which tip is designed to access the medication within a cartridge loaded in the device. The port 75 of each cavity 90 provided in the planar surface 74 allows passage therethrough of a needle tip of an injection needle assembly, which tip is designed to penetrate the injection site for fluid delivery. Ports 75 are sized larger than ports 68 to allow the main body of the injection needle assembly hub to extend down close to the lower sealing member 158, which helps reduce the height of cartridge 30. Differently sized and shaped ports are possible so long as suitable needle assembly clearance is provided while providing enough sealing surface for the sealing membranes.

Figure 6:
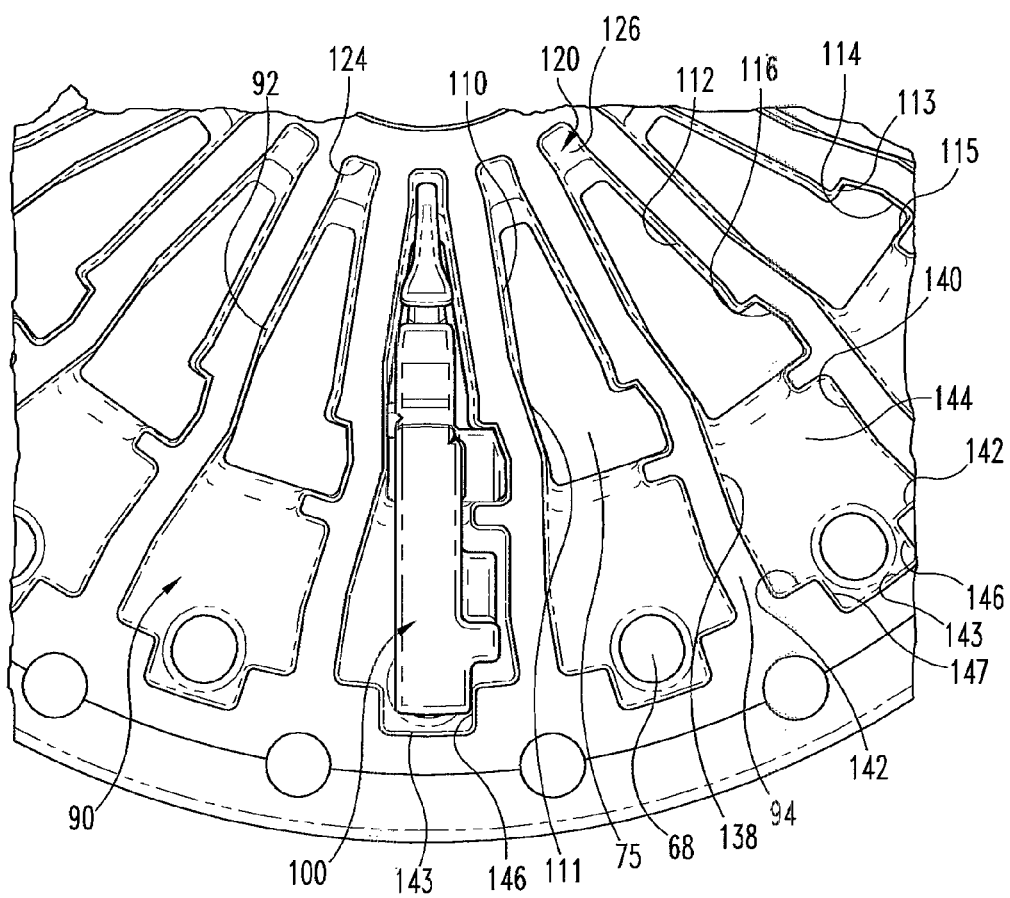
FIG. 6 is a further, partial view of the cartridge and needle assembly of FIG. 5.
Figure 7:
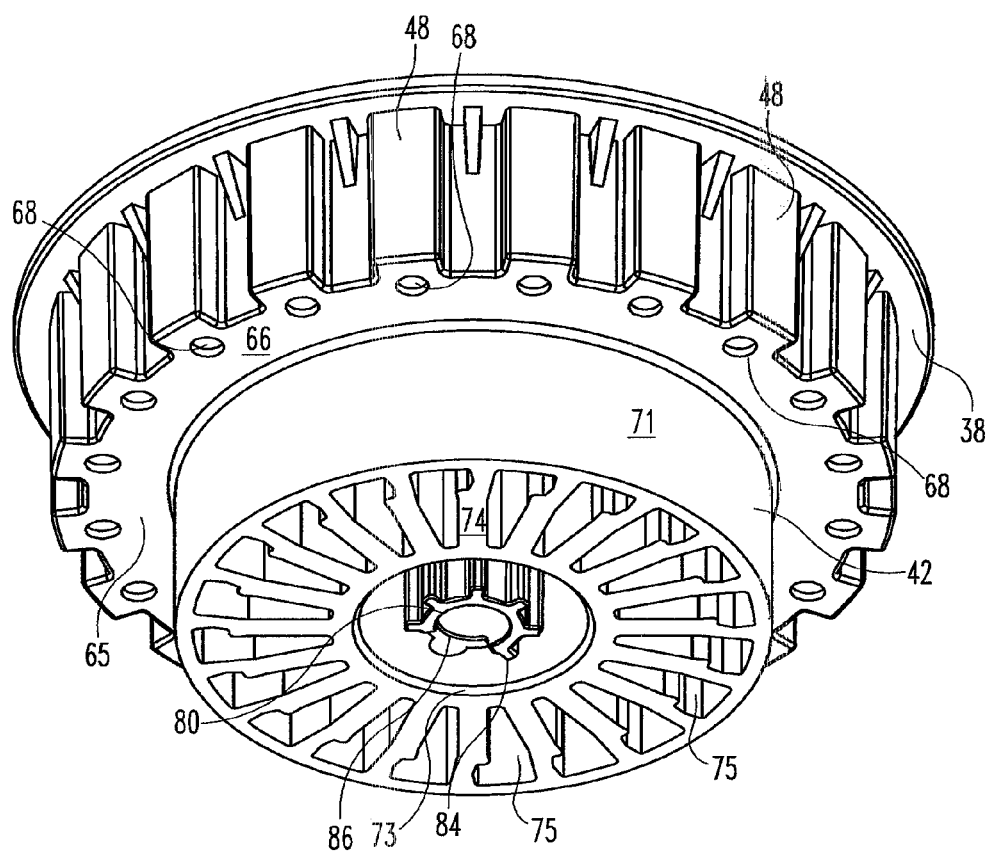
FIG. 7 is a bottom perspective view of the cartridge with injection needle assemblies of FIG. 4.
Figure 10:
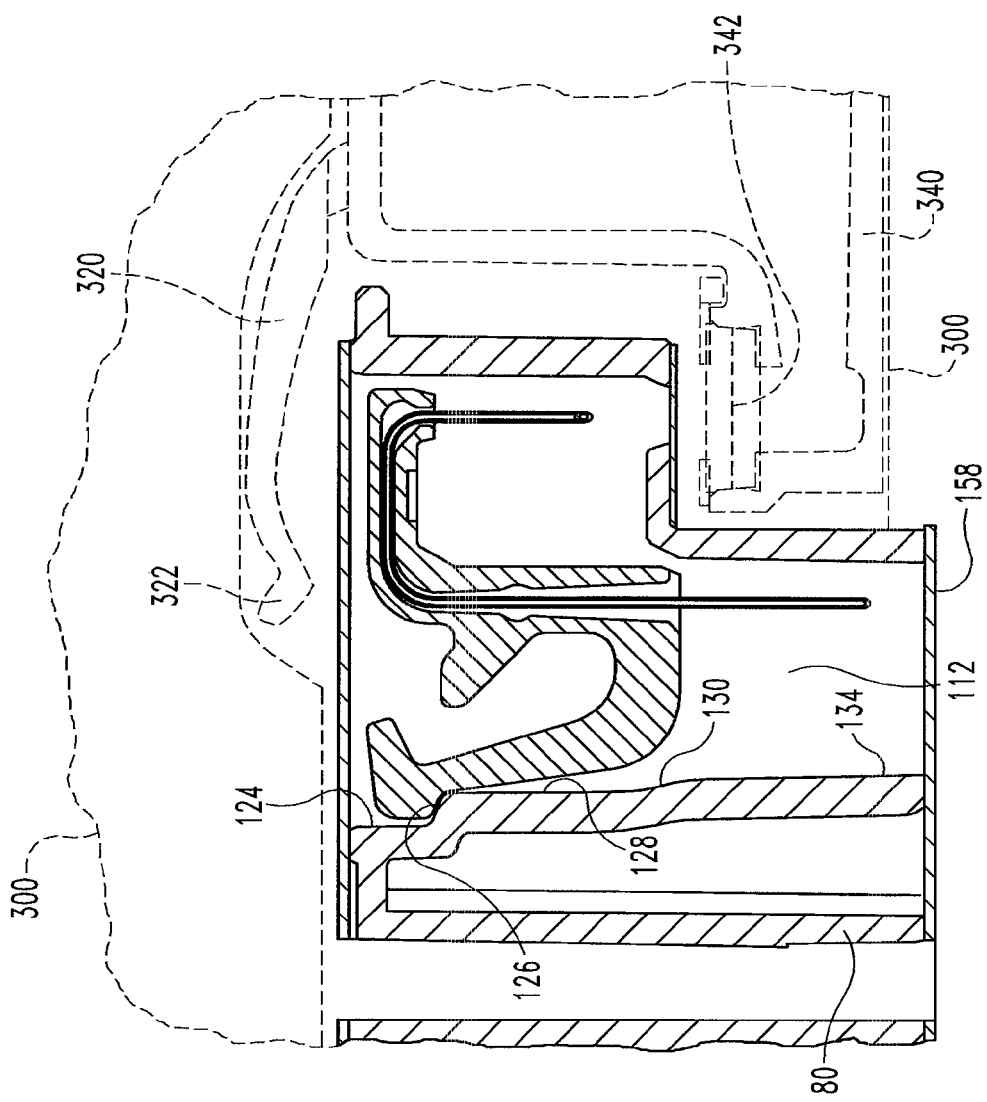
FIG. 10 is a partial cross-sectional side view of the cartridge with needle assemblies of FIG. 1 taken along line 10-10, and wherein portions of an injection device, including its medication cartridge loaded therein, with which the cartridge with needle assemblies may be used are shown in dashed lines.

With particular reference to FIGS. 6 and 10, the internal surfaces of carousel 32 that define each cavity 90 include wall portions 110, 111 and 112 that flank the angular sides and extend upward from port 75. Wall portions 110 and 112 are in clearance with the needle assembly 100. Wall portion 111 is generally parallel to centerline 60 and provides a smooth surface along which slide glides 230 and 231 of needle assembly 100. An angularly protruding section of wall portion 112 includes regions 113, 116, 114 and 115 that form an axially extending groove in which slidably fit bosses 220, 223 of needle assembly 100. The abutting relationship between wall regions 113 and 115 and bosses 220, 223 locates the needle assembly 100 within the carousel in the radial directions. Wall regions 116 and 114 are in clearance with the bosses 220, 223.

A tang-controlling wall portion, generally designated 120, of the cavity defining carousel internal surfaces connects wall portions 110 and 112 and is located radially inward therof. Wall portion 120 forms the most radial inward section of the cavity and along its vertical extent includes a lead-in section 124, a sloped camming section 126, a support section 128, a further camming section 130, and a base section 134.

Lead-in section 124 is generally vertically oriented and begins at mouth portion 92 and has a lower end that it transitions to the radially inward end of first camming section 126. Camming section 126 is designed in conjunction with the needle assembly to prevent inadvertent downward needle movement, or what is known as a dropped needle, prior to a particular needle being purposely shifted for use by the injection device. Camming region 126 is disposed at a downward angle of about twenty-five degrees from horizontal and extends to provide a majority, such as about eighty percent, of the travel of the hub spring arm described below which is produced by the camming sections 126 and 130. The shallow slope of camming region 126 coupled with its length and the strength of the resilient hub spring arm aids in resisting a dropped needle. Camming section 126 transitions at its bottom and radially outer extent to a generally vertically arranged support section 128 that has a slight slope, such as approximately 0.5 degrees, for molding purposes. Support section 128 maintains in a biased inward arrangement the needle assembly hub portion that slides therealong after being shifted inward by camming section 126 during plunging of the injection needle within that cavity. Camming section 130 curves inward, with a radius of curvature that is the center of rotation for the injection device drive member that reciprocates during its plunging and retraction along an arcuate path. Camming section 130 cams the hub spring arm further inward at a point in the pivoting motion of the drive member at which the drive member hammer described below begins to otherwise move radially outward or away from spring arm. A generally vertically arranged base section 134 that includes a slight slope for molding continues from the lower end of camming section 130 extends to form part of the port 75 at the carousel base.

The internal surfaces of carousel 32 that define cavity 90 also include wall portions radially outward of wall portions 111 and 112 including vertically extending wall portions 138 and 140 and 142 that are bounded on their lower ends by a upward facing, horizontally extending surface 144. Wall portion 142 forms the radial outward end of cavity 90 and includes a notch shape 143 that defines angular end faces 146 and 147. End face 146 is abutted by the needle hub and aids in locating needle assembly 100 in the angular direction to position the septum-piercing needle described further below. End face 147 is in clearance with the needle hub. Surface 144, which serves as a stop abutment in this shown embodiment for stopping the downward travel of the injection needle assembly, is formed by the upper surface of flange 65. Wall portion 140 forms a vertical channel in which fits in clearance with lateral projection 210 of the injection needle assembly.

The sealing of the cavities 90 to maintain sterility of the unused injection needle assemblies 100 housed therein is provided by three different sealing membranes that cover all the openings to the cavities. A first or upper sealing member 150 protectively covers the top of each cavity 90 by sealing to carousel top surface 94 around each mouth portion 92. A second or middle sealing member 154 is provided in the form of an annulus and seals to carousel surface 66 around each port 68. A third or bottom sealing member 158 is provided in the form of a smaller diameter annulus and seals to carousel surface 74 around each port 75. Central holes provided in seals 150 and 158 are used in the cartridge manufacturing process.

Different materials as are known in the art may be used for each of the sealing membranes. One suitable material for the sealing membrane 150 is a thirty micron thick aluminum sheet or foil having a heat activated glue on one side for adhesion to the carousel surface 94. A suitable material for the sealing members 154 and 158 is an acrylic copolymer membrane known as Versapor® 1200R available from Pall Corporation that is heat sealed to the carousel surfaces.

With additional reference to FIGS. 12, 13, 14 and 15, one of the injection needle assemblies 100 that is installed in each of the cavities 90 is further shown. Needle assembly 100 includes a generally J-shaped needle or cannula 160 and a support hub 162.

Cannula 160 is formed from a single, straight thirty gauge regular wall cannula. That cannula is provided with two approximately ninety degree bends along its length to form a first leg segment 164 and a second leg segment 166 that are mutually parallel and with tips that point in the same direction, namely downward in FIGS. 12-15. These leg segments may be lubricated as is known in the art, such as with silicon oil. Alternate types of lubrication may also be used, such as the use of the TriboGlide® system available from TriboFilm Research Inc. Cannula leg segment 166 is of sufficient length to administer an injection into the subcutaneous tissue of a person, and is intended to extend about 5.7 mm beyond the bottom of the carousel when fully plunged therein.

The spanning segment 168 of the cannula that spans and fluidly connects legs 164 and 166 is shown being straight, but could be formed with a different shape in different manufacturing techniques. Needle segment 164 includes a beveled tip 170 adapted for piercing an elastomeric sealing septum of a medication container for use with the injection device. During manufacture, each cannula 160 is bent with its beveled tip 170 being in a known orientation such that each injection needle assembly 100 of the cartridge 30 has a similarly arranged tip that may reduce coring of the medication container septum as that septum experiences piercings by multiple needles during successive uses of the device. The beveling of tip 170 faces in the counterclockwise direction from the perspective of a person viewing the cartridge from above. Needle segment 166 includes a beveled tip 172 adapted for piercing the skin of a user, which beveling faces in the clockwise direction from the perspective of a person viewing the cartridge from above. The bevelings may be as known in the art, such as a single grind for tip 170 and a triple grind for tip 172.

Support hub 162 includes a needle supporting base 180, and a spring arm including a radially projecting flange 182 with a more flexible, upstanding arm part 184 topped with a tang 186. Support hub 162 is made of a sufficiently rigid yet resilient plastic material, such as SAN, to support the needle while allowing for a bending of the hub spring arm. To facilitate the sliding of the support hub 162 within the carouse 132, the material comprising the hub 162 can be compounded with a silicon oil, or can be otherwise lubricated such as via TriboGlide®.

Base 180 includes a horizontal leg 190 and a vertical leg 194. A continuous channel 196 formed in the side faces 191 and 195 of legs 190 and 194, respectively, receives cannula 160 therein. An adhesive, such as a UV-cured, low viscosity glue is used to secure cannula 160 to base 180 in channel 196, and enlarged areas 198 and 200 of channel 196 are where this adhesive is applied during manufacture, which adhesive then by capillary action moves along the needle to further adhere it to the hub.

A top surface 202 of hub leg 190 is flat and horizontally oriented and forms the uppermost extent of base 180. The bottom surface of hub leg 190 includes a bottom surface region 204 that is flat and horizontally oriented, and depending region 206 that provides a vertical extension for supporting the cannula. In this embodiment, surface region 204 contacts the upper face of carousel flange 65 during use of a needle assembly to halt that needle assembly insertion, and when so halted depending region 206 fits with clearance within port 68. A projection 210 that includes a taller region 211 and a radially extending, shorter region 212 projects laterally from the side face 214 of leg 190 opposite the channeled side face 191. Projection 210 is used in the manufacturing process to maintain a proper stacked orientation of multiple hubs and multiple needle assemblies. Although shown as flush with surface region 204, projection region 212 may be shifted up to be flush with top surface 202.

A pair of cylindrical guide bosses 220 and 223 laterally project from side surface 195 of base leg 194. Beveled lateral faces 221, 224 of the bosses 220, 223 match the angling of corner 116 of wall region 114. Bosses 220 and 223 are in clearance of wall regions 114 and 116. The bottom surface of boss 223 is beveled to aid in assembly of the needle assembly into the carousel.

Bosses 220 and 223 are offset in the radial direction from each other to reduce tilting of the needle assembly in a plane extending radially within the cartridge. Bosses 220 and 223 move within the groove defined by wall regions 113-116, with one boss sliding wall region 113 and the other boss sliding along wall region 115, to guide the vertical, linear travel of the injection needle assembly 100 during its insertion and retraction. Glides 230, 231 formed on side surface 195 of base leg 194 provide contact points for sliding engagement with the cavity wall surface 111 and aid in keeping hub 162 on the centerline 60 during needle assembly plunging and retraction.

A ledge, generally designated 240, of needle hub 162 is disposed radially inward of hub vertical leg 194 within the gap 260 between hub leg 194 and hub arm 184. Ledge 240 is integrally formed with and protrudes radially inward from leg 194. Ledge 240 includes an upper face including a recessed or concave surface region 242, adjacent hub leg 194, and a drive member engageable push surface 244. Push surface 244 is the surface of the injection needle assembly 100 on which the drive member or hammer of the injection device pushes to drive the needle assembly down within the cavity 90 during use as further described below. Ledge surface region 242 is located outward of push surface 244 and its shape provides clearance for a membrane cutting surface of the injection device drive member hammer as the hammer otherwise contacts push surface 244 as the drive member sweeps down during its activation.

Push surface 244 is generally flat and oriented horizontally, resulting in it facing upward and being parallel to needle spanning segment 168. Push surface 244 is located at a height below the cannula segment 168, and also is located at a height below the lowest extent of hub leg 190, which in the shown embodiment is at region 206 at which needle segment 164 projects down from the hub in a completely exposed condition.

Ledge 240 includes a squared-off end 248 at the most radially inward extent of push surface 244. A sloping bottom surface 250 of ledge 240 extends from end 248 to hub leg 190. The generally triangular shape of ledge 240, from the perspective of a FIG. 13 viewer, results in a rigid ledge that will bear the hammer forces applied thereto during use. Other overall shapes of the ledge may be employed so long as a suitable push surface is provided without compromising the successful functioning of the hub.

The flange 182 of support hub 162 is rigid and integrally formed with the bottom end of hub leg 194. The upstanding hub arm part 184 is integrally formed with the radially inward end of flange 182 and tapers in thickness as it extends upward therefrom. Flange 182 and the bottom end of hub arm part 184 are disposed directly below and in vertically spaced apart relationship with ledge 240. As it extends upward, hub arm 184 extends radially inward at a slight angle, such as about eight degrees from vertical with respect to its radial inner surface and seventeen and one half degrees from vertical with respect to its radial outer surface. Due to this angling, along with the arm positioning on the inward extent of the flange, a radial gap 260 results between the radial outer surface of arm 184 and hub leg 194, which gap 260 increases in size as it extends vertically upward. The shape, size and construction of the arm 184 results in the arm having the flexibility to allow it to function as a spring arm. This flexibility is sufficient for it to be cammed radially outward as described below during use toward hub leg 194 so as to elastically decrease the size of radial gap 260.

The radially inward face of arm 184 includes a contoured projection 266 at its upper end. Projection 266 includes a ramping surface 268 at its lower region which transitions to a generally vertically aligned hold surface 270 at its upper region. Ramping surface 268 and hold surface 270 are sized and shaped complementary to camming section 126 and lead-in section 124 of cavity wall portion 120. This complementary design, and in view of the spring arm effect of hub arm 184, causes the hub projection 266 to fit against the cavity wall portion 120 to retain the needle assembly 100 in an upward, or non-plunged, arrangement in the carousel cavity 90.

The radially outward face of arm 184 at its upper end and at a location opposite the contoured projection 266 includes the hammer-engaging tang 186 of hub 162. As it projects from hub arm 184 to extend outward into a space above gap 260, tang 186 enlarges laterally to form tips 272, 274 that are in clearance with cavity wall surfaces 110, 112 but which prevent the drive member hammer from passing between the tang 186 and cavity wall.

A lower surface portion or underside portion 284 of tang 186 is used to directly engage the injection device hammer to enable needle assembly retraction as described below. Tang underside portion 284 that engages the injection device hammer to serve as a pull surface is generally flat. When the hub arm 184 is cammed outward during needle assembly plunging into its needle assembly lifting arrangement, the tang pull surface 284 is disposed directly above and in vertically spaced apart relationship with ledge 240, and in particular ledge push surface 244. In this arrangement, the tang pull surface 284 is disposed at a height below the upper surface 202 of hub leg 190 as well as below the height of cannula segment 168.

Figure 11:
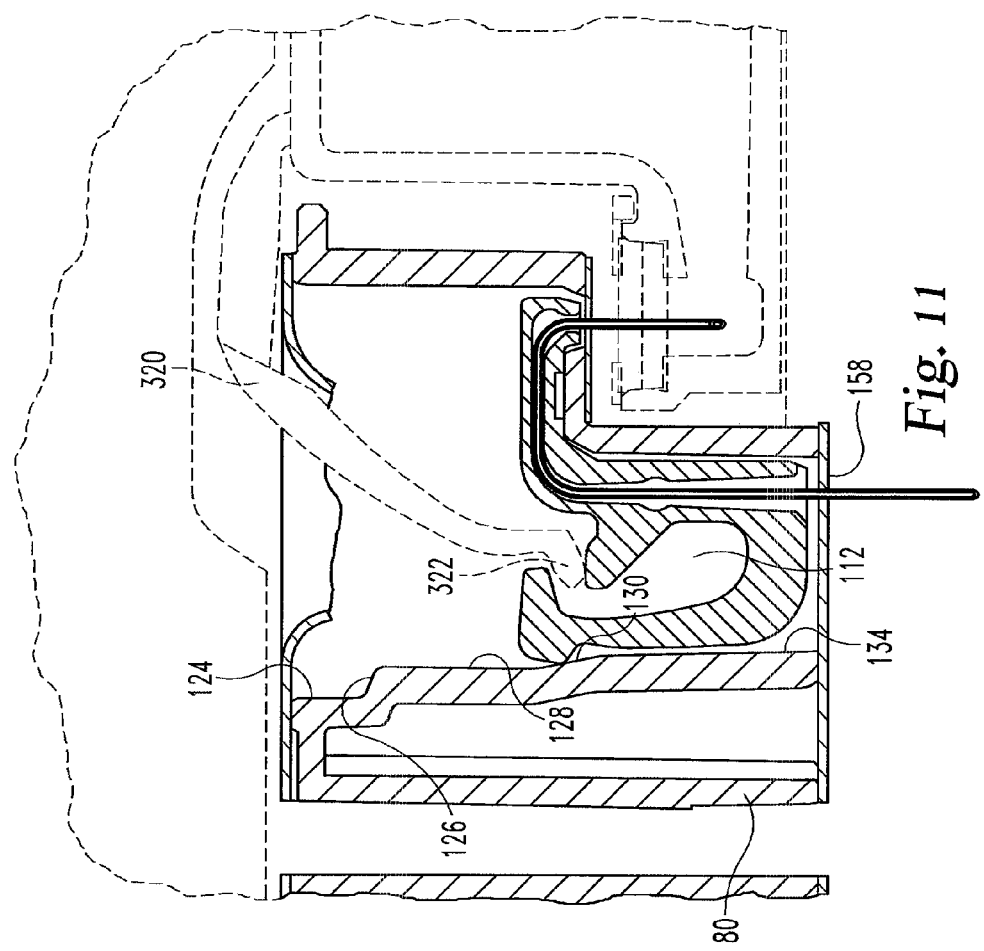
FIG. 11 is a cross-sectional side view similar to the view of FIG. 10 after the needle assembly aligned with the injection device drive member has been driven from its retracted arrangement to its plunged, delivery arrangement.
Figure 12:
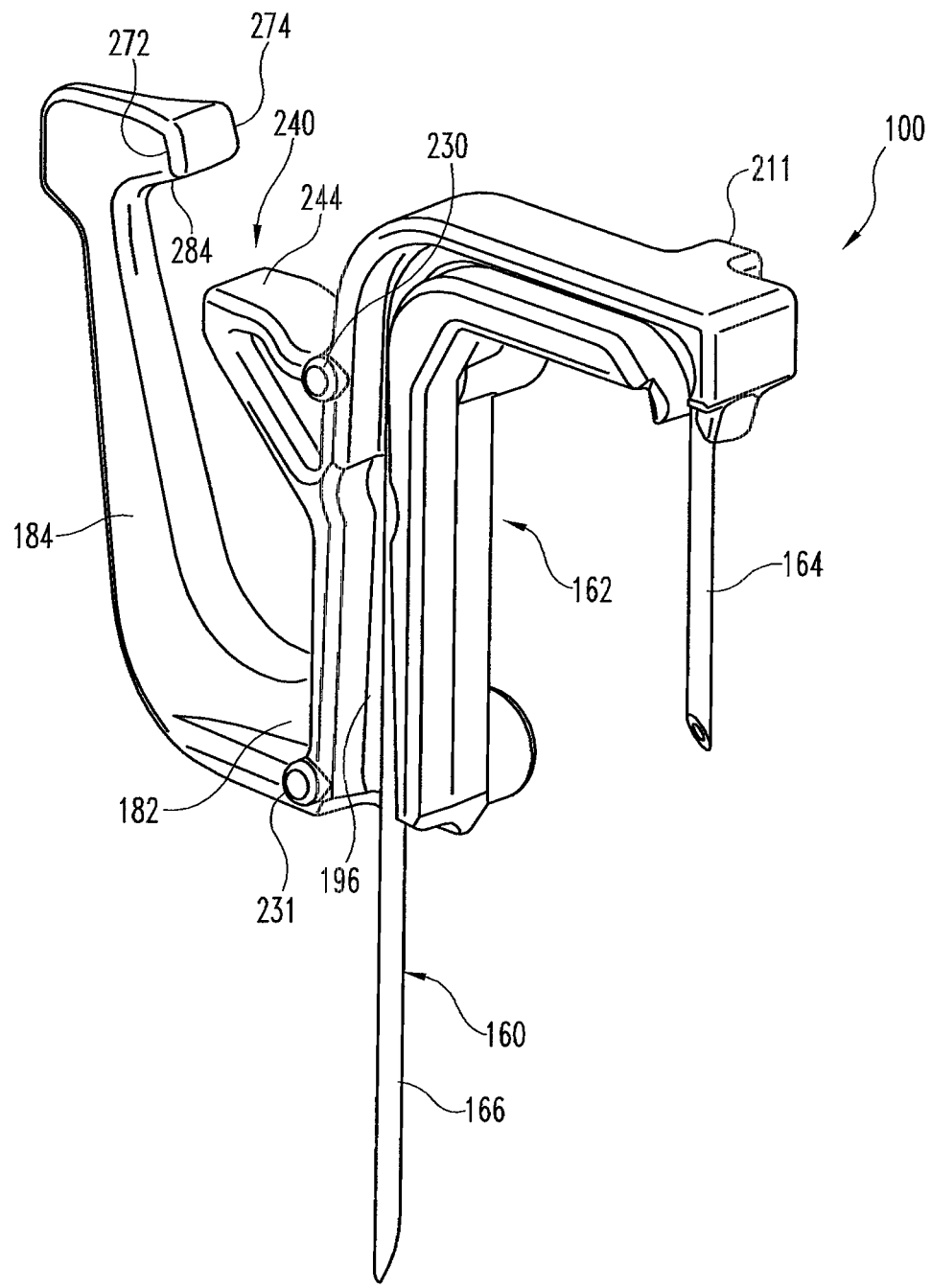
FIG. 12 is a perspective view of the injection needle assembly of FIG. 5 removed from the cartridge carousel.
Figure 13:
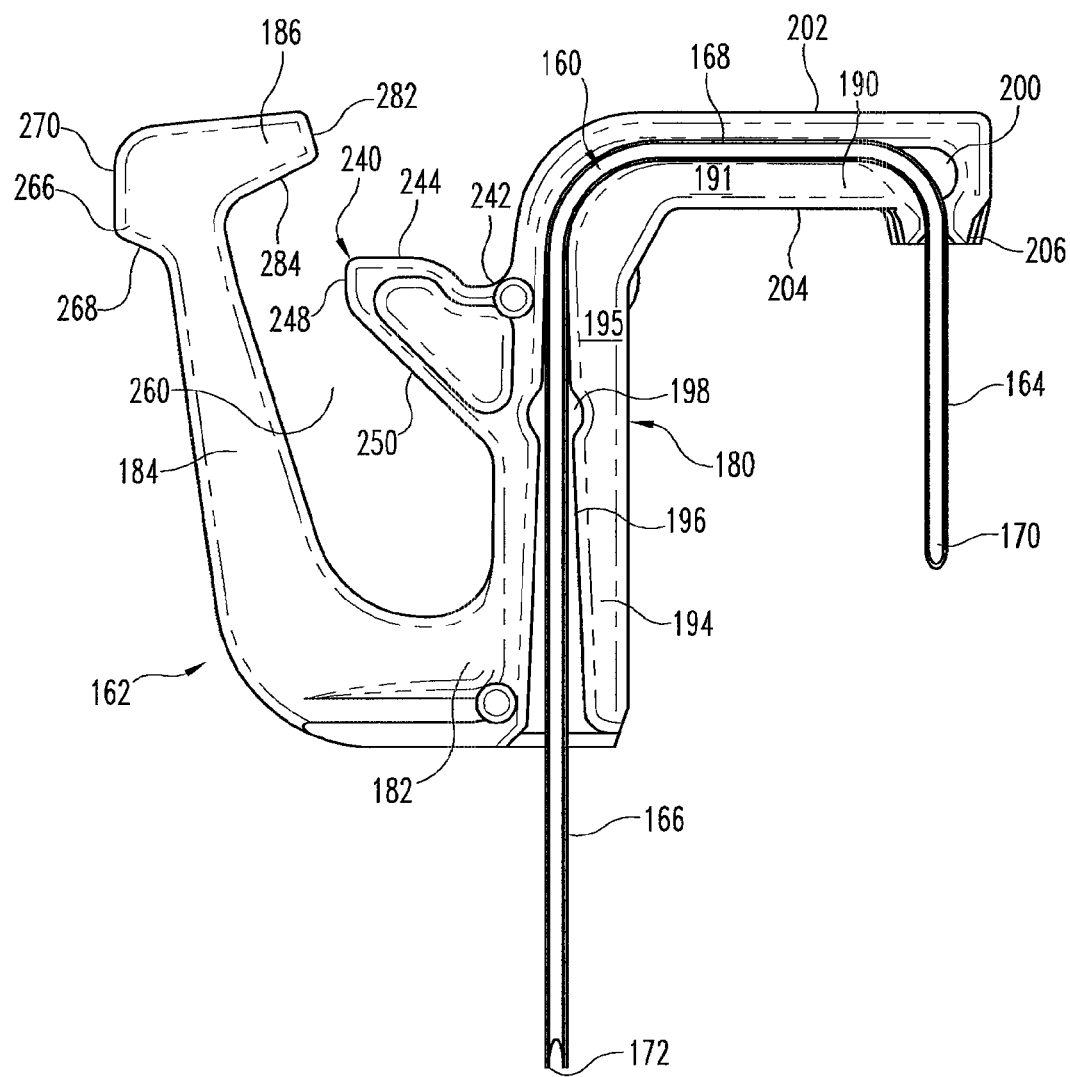
FIG. 13 is a side view of the injection needle assembly of FIG. 12.
Figure 14:
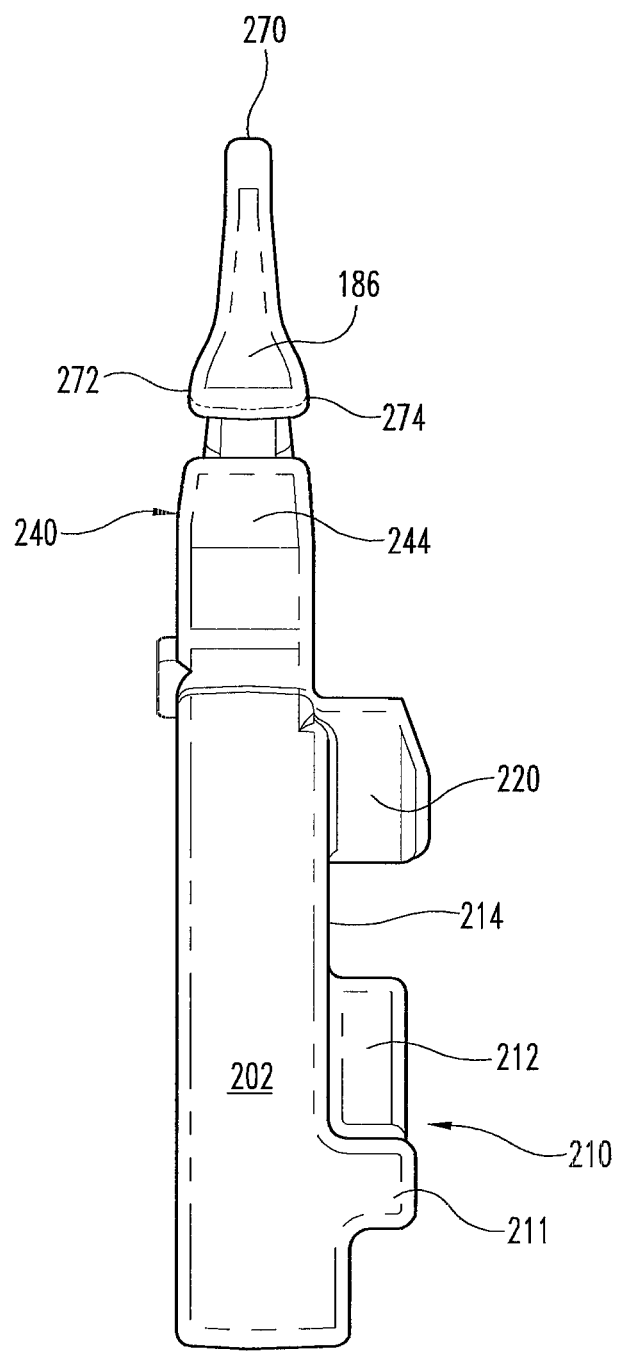
FIG. 14 is a top view of the injection needle assembly of FIG. 12.
Figure 15:
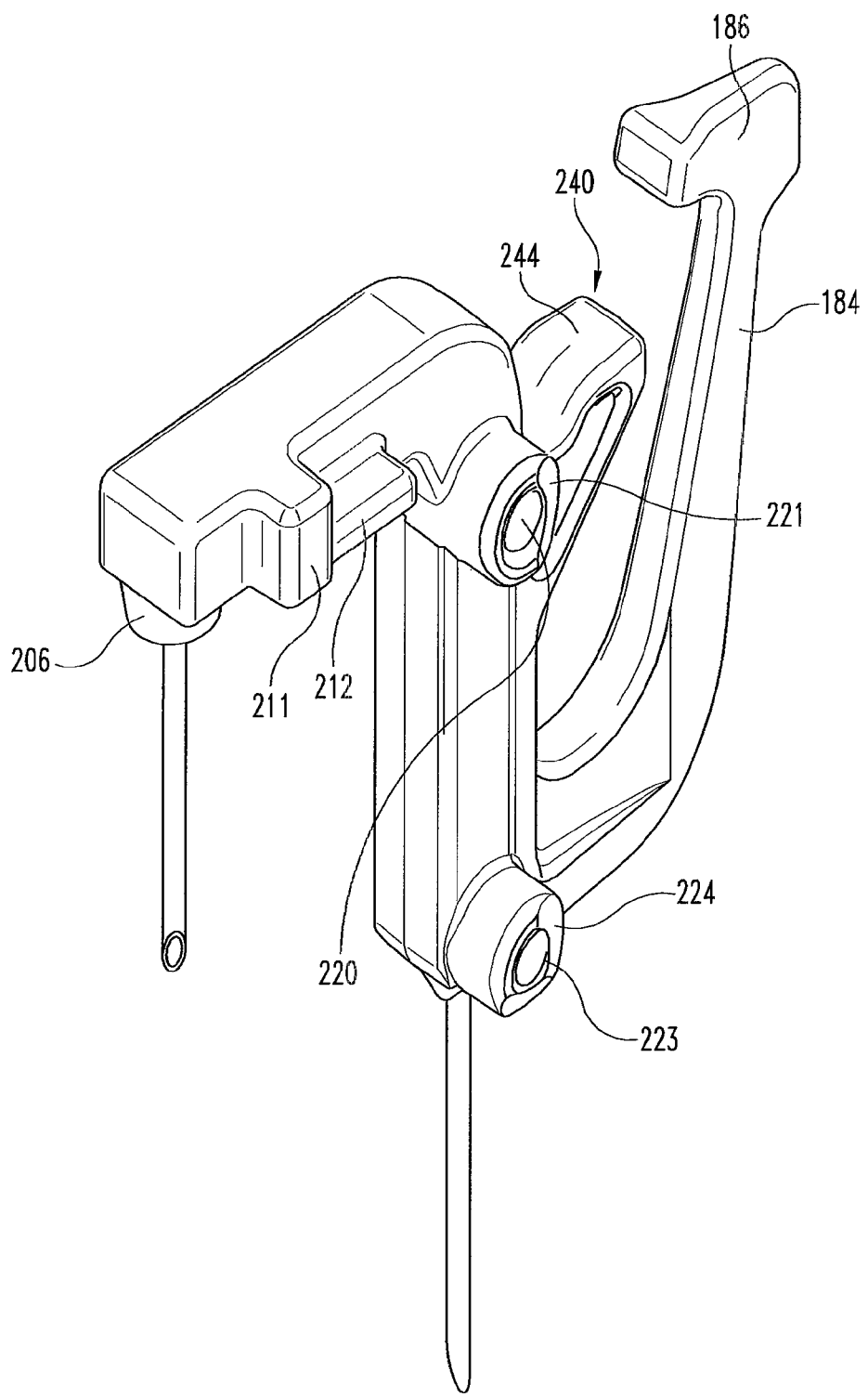
FIG. 15 is an opposite perspective view of the injection needle assembly of FIG. 12.

With additional reference to FIGS. 10 and 11, cartridge 30 will be further explained as to its operation. A partially shown cartridge 30 is shown in FIG. 10 loaded into an injection device shown partially and in dashed lines. The injection device, generally outlined at 300, is shown including a drive member or hammer 320 with a head 322, and a medication-filled cartridge 340 including a pierceable septum 342 which is loaded within the injection device. Portions of the injection device that retain the needle cartridge 30 therein are not shown to facilitate illustration. The hammer 320 is pivotably shifted within the device via a motorized drive system of the device to plunge and then return the needle assembly during use. In FIG. 10, the needle assembly 100 is located beneath the hammer 320 in a ready or non-plunged arrangement. In this arrangement, tang 186 is clear of the space directly above ledge push surface 244. When the injection device 300 is operated for an injection, hammer 320 swings downward in an arcuate path, initially causing the hammer head 322 to pierce seal 150 and make direct abutting contact with ledge push surface 244. Tang 186 is not contacted by the hammer during this downward motion. After contacting push surface 244 and in a continuous motion, hammer 320 continues to swing downward to force ledge 240 and the rest of the needle hub 162, along with the hub-retained cannula 160, downward. During this pivoting hammer travel, hammer head 322 slides along the push surface 244 as the needle assembly 100 travels vertically. As needle assembly 100 moves downward to its plunged arrangement shown in FIG. 11, resilient arm 184 pivots or bends radially outward toward hub leg 194, shortening gap 260, as projection 266 first slides along and is cammed radially outward by cavity wall region 126, then slides along in a maintained arrangement by cavity wall region 128, and then is further cammed radially outward by cavity wall region 130. Projection 266 is in contact with wall region 130 at the point when the needle assembly is fully plunged, at which point the radially outward movement of bending arm 184 has carried tang 186 to an adjacent position directly above, but in spaced apart relationship due to tolerances, the hammer head 322 as shown in FIG. 11.

After the device completes its injection by forcing medication in cartridge 340 into the needle tip 170 that has pierced septum 342 and through the cannula segments and out needle tip 172, injection device 300 reciprocates the hammer 320 so it swings upward to its ready position within the injection device. During the hammer return, the tang pull surface 284 is directly engaged by the upward facing surface of hammer head 322, which engagement effectively lifts the needle assembly 100 upward within carousel 32. The needle assembly 100 is lifted by the drive member until the tang 186, due to the hub arm resiliency, moves back radially inwardly clear of engagement with the hammer head 322 as the hub arm projection 266 reaches and slides upward along the camming region 126, which projection sliding pulls needle assembly 100 up toward its original retracted position, such that even though the tang disengages from the hammer head 322 before the needle assembly 100 reaches its fully retracted position, the needle assembly retraction will continue as necessary for the needle assembly to reach, or be close to reaching, its original pre-plunged position, at which point the camming region and hub arm interface satisfactorily to maintain the needle assembly so that the needle tips 170 and 172 do not extend or drop down too low within the carousel 32 to a position extending from the ports 68 and 75 which would compromise further device operation.

Before the next injection, injection device 300 rotates cartridge 30 within the device via the interface of the device indexing mechanism and carousel wall region 40 so that the next injection needle assembly 100 within the cartridge 30 can be similarly used with the hammer 320 in the next injection.

Figure 16:
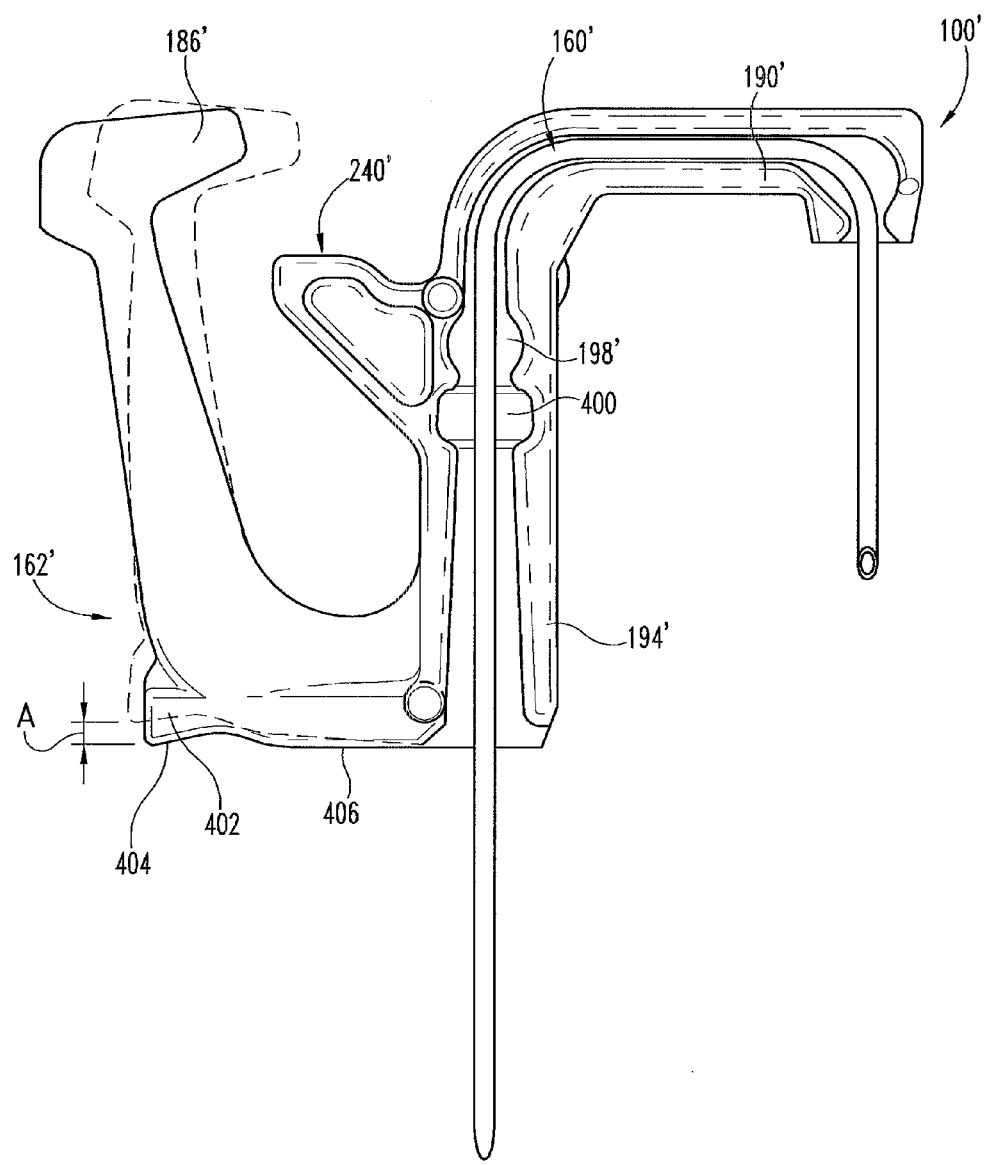
FIG. 16 is a side view, similar to the view of FIG. 13, of an alternate injection needle assembly that can used as part of a cartridge of the present invention, wherein the hub spring arm is also shown in dashed lines in a cammed-in configuration.
Figure 17:
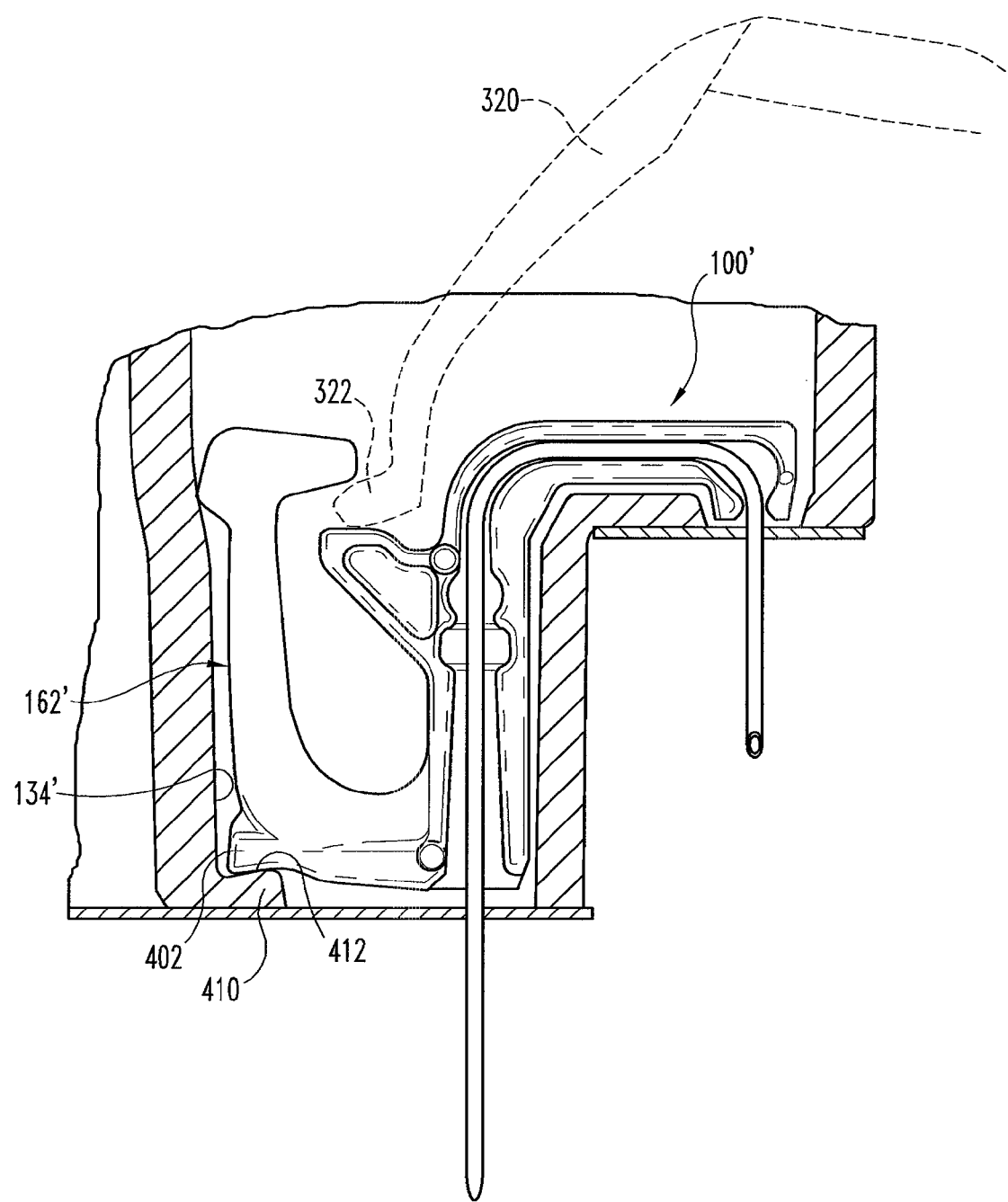
FIG. 17 is a partial cross-sectional side view of a cartridge with a needle assembly of the type shown in FIG. 16, with the shown needle assembly in its plunged, delivery arrangement.

Referring now to FIGS. 16 and 17, portions of an alternate embodiment of the needle cartridge of the present invention are shown. This needle cartridge is similar in most respects to the cartridge described above with respect to FIGS. 1-15 as will be recognized by one of skill in the art, but is different in ways as described below.

As shown in FIG. 16, the needle assembly 100' includes a needle 160' and a support hub 162'. The hub spring arm including tang 186' is shown in solid lines in its arrangement when needle assembly 100' is in its retracted position within the cartridge carousel, and in dashed lines in its arrangement when needle assembly 100' is in its delivery position.

The hub includes horizontal leg 190' from which ledge 240' projects, and a vertical leg 194. Ledge 240' and tang 186' are engaged by head 322 of drive member 300 in the same fashion as their counterparts in the embodiment of FIGS. 1-15. A recess 400 formed in the hub channel in which the cannula 160' is received is disposed below glue application area 198'. Recess 400 serves as a glue stop that interrupts capillary action associated with glue application during manufacture such that the cannula portion directly below recess 400 is not at that point adhered to the hub.

The stopping of the downward travel of needle assembly 100' at its delivery position during needle plunging is provided with a stop protuberance formed on the hub spring arm. At the delivery position shown in FIG. 17, the hub leg 190' is in clearance with the surface defining the base of the cavity of the carousel.

The stop protuberance is indicated at 402 and projects radially inward, or away from the base hub including leg 194', from the spring arm. Protuberance 402 includes a downward facing surface 404 that reaches downward as it extends away from the spring arm nearly to the base 406 of the hub. Protuberance 402 is formed along a bottom end region of the spring arm, and when the spring arm bends while moving from the ready arrangement shown in solid lines in FIG. 16 to the needle assembly lifting arrangement shown in dashed lines in FIG. 16, protuberance 402 moves upward relative to the hub portion including hub leg 194'. The extent of this upward movement is indicated at "A" in FIG. 16. This movement allows for the complementary stop portion of the carousel support to be disposed at a higher height therein.

As shown in FIG. 17, the needle assembly support includes a stop shoulder 410 that projects into the cavity in which needle assembly 100' is shiftably mounted. Stop shoulder 410 is formed at the bottom end of cavity wall base section 134' and therefore is disposed at a furthermost extent of the needle assembly support in the downward direction. Stop shoulder 410 includes an angled upper surface 412 that is engaged in an abutting fashion by the protuberance surface 404 to positively or completely halt shifting of the needle assembly 100' at the delivery position shown in FIG. 17.

While this invention has been shown and described as having multiple designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A cartridge for a medication injection device having a reciprocating drive member, the cartridge comprising:
a plurality of injection needle assemblies, each injection needle assembly including a hub and a needle, each said needle including a first leg segment with a first end and a second leg segment with a second end and a spanning segment, said spanning segment providing fluid communication between portions of said first leg segment and said second leg segment opposite said first and second ends, said first end and second end of each said needle both facing in a first direction, each said hub including a first portion and a second portion, said needle supported in said first hub portion, said second hub portion movable relative to said first hub portion between a ready arrangement and a needle assembly lifting arrangement;

a needle assembly support defining a plurality of mutually parallel, needle assembly accommodating cavities, each injection needle assembly mounted in a different one of said plurality of needle accommodating cavities to be shiftable in the first direction from a retracted position, at which said first and second ends both are disposed within said cavity, to an injection position, at which said first and second ends both project outside of said cavity, said needle assembly support loadable into the injection device to be movable therein to allow for separate operational alignment of each injection needle assembly with the drive member of the injection device, whereby the drive member may move to drivingly engage the hub of an operationally aligned needle assembly so as to shift that needle assembly from the retracted position to the injection position;

each said needle assembly structured and arranged with said needle assembly support for its second hub portion to be moved relative to its first hub portion from said ready arrangement to said needle lifting arrangement upon a shifting of that needle assembly from the retracted position to the injection position;

wherein each said second hub portion includes a pull surface engagable with the drive member during needle assembly lifting;

wherein for a given needle assembly in alignment for operational engagement with the drive member, and when the drive member drivingly engages the hub of that given needle assembly, said second hub portion pull surface, in a second direction opposite the first direction, is located clear of the drive member when said given needle assembly is disposed in the retracted position with said second hub portion in the ready arrangement;

wherein for that given needle assembly, said second hub portion pull surface, in the second direction, is located adjacent the drive member when said given needle assembly has been shifted to said injection position by said hub being engaged by the drive member moving in the first direction, whereby said given needle assembly is liftable in said second direction by engagement of said pull surface of said second hub portion in the needle assembly lifting arrangement by the drive member when the drive member returns in the second direction;

wherein the improvement comprises a hub ledge having a drive member engageable push surface projecting within a gap between said first hub portion and said second hub portion, and wherein said second hub portion pull surface, when said second hub portion is in the needle assembly lifting arrangement, is disposed at a height in the first direction below a height of a furthermost extent of said first hub portion in said second direction; and wherein said ledge is integrally formed with said first hub portion and further includes a recessed region between said drive member engageable push surface and said first hub portion, said ledge recessed region providing clearance for a membrane cutting surface of the drive member.

2. The cartridge of claim 1 wherein said drive member engageble push surface is disposed at a height in the first direction below a height of said needle spanning segment.

3. A cartridge for a medication injection device having a reciprocating drive member, the cartridge comprising:

a plurality of injection needle assemblies, each injection needle assembly including a hub and a needle, each said needle including a first leg segment with a first end and a second leg segment with a second end and a spanning segment, said spanning segment providing fluid communication between portions of said first leg segment and said second leg segment opposite said first and second ends, said first end and second end of each said needle both facing in a first direction, each said hub including a first portion and a second portion, said needle supported in said first hub portion, said second hub portion movable relative to said first hub portion between a ready arrangement and a needle assembly lifting arrangement;

a needle assembly support defining a plurality of mutually parallel, needle assembly accommodating cavities, each injection needle assembly mounted in a different one of said plurality of needle accommodating cavities to be shiftable in the first direction from a retracted position, at which said first and second ends both are disposed within said cavity, to an injection position, at which said first and second ends both project outside of said cavity, said needle assembly support loadable into the injection device to be movable therein to allow for separate operational alignment of each injection needle assembly with the drive member of the injection device, whereby the drive member may move to drivingly engage the hub of an operationally aligned needle assembly so as to shift that needle assembly from the retracted position to the injection position;

each said needle assembly structured and arranged with said needle assembly support for its second hub portion to be moved relative to its first hub portion from said ready arrangement to said needle lifting arrangement upon a shifting of that needle assembly from the retracted position to the injection position;

wherein each said second hub portion includes a pull surface engagable with the drive member during needle assembly lifting;

wherein for a given needle assembly in alignment for operational engagement with the drive member, and when the drive member drivingly engages the hub of that given needle assembly, said second hub portion pull surface, in a second direction opposite the first direction, is located clear of the drive member when said given needle assembly is disposed in the retracted position with said second hub portion in the ready arrangement;

wherein for that given needle assembly, said second hub portion pull surface, in the second direction, is located adjacent the drive member when said given needle assembly has been shifted to said injection position by said hub being engaged by the drive member moving in the first direction, whereby said given needle assembly is liftable in said second direction by engagement of said pull surface of said second hub portion in the needle assembly lifting arrangement by the drive member when the drive member returns in the second direction;

wherein the improvement comprises a hub ledge having a drive member engageable push surface projecting within a gap between said first hub portion and said second hub portion, and wherein said second hub portion pull surface, when said second hub portion is in the needle assembly lifting arrangement, is disposed at a height in the first direction below a height of a furthermost extent of said first hub portion in said second direction; and wherein said drive member engageble push surface is arranged perpendicular to said first direction and is disposed at a height in said first direction below a point at which said needle first leg segment depends in said first direction completely exposed from said first hub portion.

4. A cartridge for a medication injection device having a reciprocating drive member, the cartridge comprising:

a plurality of injection needle assemblies, each injection needle assembly including a hub and a needle, each said needle including a first leg segment with a first end and a second leg segment with a second end and a spanning segment, said spanning segment providing fluid communication between portions of said first leg segment and said second leg segment opposite said first and second ends, said first end and second end of each said needle both facing in a first direction, each said hub including a first portion and a second portion, said needle supported in said first hub portion, said second hub portion movable relative to said first hub portion between a ready arrangement and a needle assembly lifting arrangement;

a needle assembly support defining a plurality of mutually parallel, needle assembly accommodating cavities, each injection needle assembly mounted in a different one of said plurality of needle accommodating cavities to be shiftable in the first direction from a retracted position, at which said first and second ends both are disposed within said cavity, to an injection position, at which said first and second ends both project outside of said cavity, said needle assembly support loadable into the injection device to be movable therein to allow for separate operational alignment of each injection needle assembly with the drive member of the injection device, whereby the drive member may move to drivingly engage the hub of an operationally aligned needle assembly so as to shift that needle assembly from the retracted position to the injection position;

each said needle assembly structured and arranged with said needle assembly support for its second hub portion to be moved relative to its first hub portion from said ready arrangement to said needle lifting arrangement upon a shifting of that needle assembly from the retracted position to the injection position;

wherein each said second hub portion includes a pull surface engagable with the drive member during needle assembly lifting;

wherein for a given needle assembly in alignment for operational engagement with the drive member, and when the drive member drivingly engages the hub of that given needle assembly, said second hub portion pull surface, in a second direction opposite the first direction, is located clear of the drive member when said given needle assembly is disposed in the retracted position with said second hub portion in the ready arrangement;

wherein for that given needle assembly, said second hub portion pull surface, in the second direction, is located adjacent the drive member when said given needle assembly has been shifted to said injection position by said hub being engaged by the drive member moving in the first direction, whereby said given needle assembly is liftable in said second direction by engagement of said pull surface of said second hub portion in the needle assembly lifting arrangement by the drive member when the drive member returns in the second direction;

wherein the improvement comprises a hub ledge having a drive member engageable push surface projecting within a gap between said first hub portion and said second hub portion, and wherein said second hub portion pull surface, when said second hub portion is in the needle assembly lifting arrangement, is disposed at a height in the first direction below a height of a furthermost extent of said first hub portion in said second direction;

wherein each said second hub portion comprises a stop protuberance projecting from a spring arm of said second hub portion, and wherein said needle assembly support includes a stop shoulder projecting into each of said needle assembly accommodating cavities for abutting engagement with said stop protuberance so as to positively halt shifting of said needle assembly at said injection position.

5. The cartridge of claim 4 wherein said stop protuberance projects away from said first hub portion and is formed along a bottom end region of said spring arm, wherein said stop protuberance, when said spring arm bends for moving said second hub portion relative to its first hub portion from the ready arrangement to the needle assembly lifting arrangement, shifts in said second direction relative to said first hub portion, and wherein said stop shoulder is disposed at a furthermost extent of said needle assembly support in said first direction.

* * * * *